United States Patent [19]

Lässer et al.

[11] Patent Number: 4,596,148
[45] Date of Patent: Jun. 24, 1986

[54] TRITIUM PRESSURE MEASUREMENT

[75] Inventors: Rainer Lässer; Karl-Heinz Klatt, both of Jülich, Fed. Rep. of Germany

[73] Assignee: KFA Kernforschungsanlage Julich, Jülich, Fed. Rep. of Germany

[21] Appl. No.: 592,241

[22] Filed: Mar. 22, 1984

[30] Foreign Application Priority Data

Mar. 26, 1983 [DE] Fed. Rep. of Germany ....... 3311194

[51] Int. Cl.⁴ .............................................. G01L 21/30
[52] U.S. Cl. ...................................... 73/753; 324/461
[58] Field of Search ....................... 73/753, 30, 19, 23; 324/460, 461; 313/54

[56] References Cited

U.S. PATENT DOCUMENTS 2,968,730 1/1961 Morris et al. .......................... 313/54
3,797,299 3/1974 Nelson et al. ............................ 73/19

FOREIGN PATENT DOCUMENTS 845273 7/1952 Fed. Rep. of Germany .

Primary Examiner—Donald O. Woodiel
Attorney, Agent, or Firm—Karl F. Ross; Herbert Dubno

[57] ABSTRACT

The total pressure of pure tritium or the partial pressure of tritium or another radioactive isotope depending upon the calibration is measured utilizing a cylindrical positive electrode, an axial central thin negative electrode coaxial with the cylindrical electrode and a source having a voltage up to 200 V connected in circuits of these electrodes. The circuit also includes a picoampere meter or a high ohmic resistance whose voltage drop is monitored by a digital volt meter so that currents of the order of picoamperes in the circuit can be detected and with appropriate calibration of the unit can provide an output which represents the pressure.

25 Claims, 4 Drawing Figures

TRITIUM PRESSURE MEASUREMENT

FIELD OF THE INVENTION

The present invention relates to a pressure measuring device for determination of total and partial tritium pressure and which is effective over a relatively wide range, e.g. from 0.1 mbar to 100 bar.

BACKGROUND OF THE INVENTION

Tritium is produced in large quantities for a variety of purposes, e.g. work in nuclear fusion, and is commercially available at tolerable cost and in high purity. As a consequence, the measurement of tritium pressure is increasingly of significance and importance.

To date, the measurement and monitoring of tritium pressure within the above-mentioned range has utilized capacitive pressure sensors working into appropriate capacitance and measuring electronic circuitry to obtain the requisite precision.

Such pressure sensors are extremely costly and can only be effective for the determination of total pressure. Perhaps an even greater problem is the mechanical instability of such pressure sensors which are highly sensitive to vibration, impact and like effects.

OBJECTS OF THE INVENTION

It is, therefore, the principal object of the present invention to provide an apparatus for the determination of tritium pressures, especially within the range of 0.1 mbar to 100 bar whereby the drawbacks of earlier systems are obviated.

A more specific object of this invention is to provide a robust, mechanically stable and highly reliable pressure measuring device which is effective over a wide pressure range in the measurement of the tritium pressures.

It is also a specific object of this invention to provide a pressure measuring device for the purposes described which is less sensitive to vibration effects than are earlier devices.

Yet another object of this invention is to provide a measuring device which can respond to the extremely important parameter, tritium partial pressure, and yet be of low cost and high precision.

SUMMARY OF THE INVENTION

These objects are attained in accordance with the invention with a pressure-measuring device comprising a housing which is formed with a cylindrical positive electrode of a large area juxtaposed with a thin negative axial electrode across which is connected a voltage source applying the positive and negative polarities respectively to these electrodes and having a voltage up to 200 V.

According to the invention, moreover, means responsive to a picoampere current flow through this circuit is provided, the latter means including a meter which can display or indicate or register this current which, we have found, is a highly linear function of the tritium pressure within the aforementioned range.

According to one embodiment of the invention a picoampere measuring ammeter, i.e. a pico-amperemeter is provided within the aforementioned circuit. Alternatively, a high-ohmic resistor (e.g. of 1 Megohm) can be included in the circuit and the meter can be a voltmeter measuring the voltage drop across this resistor.

According to a feature of the invention, the housing is provided with means enabling it to be coupled to the unit in which the tritium pressure measurement is to be taken, the latter means preferably being flanges on the housing or associated therewith. This flange or these flanges make the housing connectable to the unit in which the tritium pressure to be measured is contained and/or enable the electrode contacts or connectors to be attached to the electrodes.

Preferably, moreover, the cylindrical electrode is separable from the housing, i.e. is an independent element which can be mounted in or dismounted from the housing.

The device of the invention has been found to be effective not only for the measurement of the total pressure of pure tritium but also for the measurement of tritium partial pressure when the tritium is present with other gases in a mixture.

The system for mounting the device of the invention can be varied and the device can be utilized in in-line and off-line applications. We have found that the device of the invention costs only about one-tenth of that of a conventional capacitive tritium pressure measurement unit.

The system of the invention utilizes the fact that when the source establishes a negative potential on the central or axial thin electrode and a positive potential on the cylindrical electrode, the current which flows between them is proportional to the radioactive decay and thus is proportional to the number of tritium atoms which may be present in the space and hence to the tritium partial pressure. Apparently weakly energetic $3He^+$ ions tend to move toward the negative thin electrode while the $\beta$ particles which have an energy of about 5.9 keV tend to impinge on the large area cylindrical electrode.

The charge accummulation or transfer is, at a first approximation, independent of absolute pressure but a function of the partial pressure of tritium and only with increasing pressures does the tendency toward recombination create a potential source of error. Consequently, with the measurement of high pressures in the aforementioned range, we prefer to increase the potential which may apply across the electrodes to, say, 80 V or greater. We should note that the voltage source may supply 0 to 200 V according to the invention, the lower voltage meaning that the source is an extremely low voltage source providing a potential of less than 1 V and designed solely to measure the polarities of the two electrodes. Preferred source voltage is 80 to 120 volts.

We have also found that the spacing between the electrodes preferably should be limited to about 10 mm, i.e. should not exceed 10 mm, whereas interelectrodes spacings less than 2 mm tend to create manufacture problems. The preferred interelectrode spacing is thus 4 to 6 mm. The accumulation of charge carriers on the electrodes and hence the current can be detected by one of the sensitive current measuring systems previously mentioned. A pico-ampere measuring ammeter, of course, is such a highly sensitive current measuring device as is a voltmeter responsive to the potential difference developed across a high ohmic resistor in series with an extremely low current circuit.

An important advantage of the present invention is that the sensing unit itself can be composed of materials which can be heated to relatively high temperatures, e.g. temperatures of up to about 250° C. Therefore, the mechanical parts are bakeable to 250° C. and are ultrahigh vacuum compatible. The device can of course be standardized or calibrated at different temperatures and naturally a calibration temperature can be selected to correspond to the temperature at which measurement is made. For exact monitoring of the tritium pressure of a gas which may have a variable temperature, the monitoring circuitry can include means for automatically compensating for the temperature or for controlling the temperature at which the measurement is effected. Naturally, correction can also be made in accordance with the formula $$p = (T/T_o) \cdot p_o$$

wherein p is the pressure measurement desired;

$p_o$ is the measured pressure at absolute temperature $T_o$; and

T is the temperature for which the measurement of p is of interest.

Naturally, electronic circuitry, e.g. an amplifier can be utilized to effect the same calculation in a digital or analog system automatically. With appropriate calibration, the measuring device of the invention can, of course, be utilized for the pressure measurement of other gaseous radioactive isotopes or isotope mixtures.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 1:
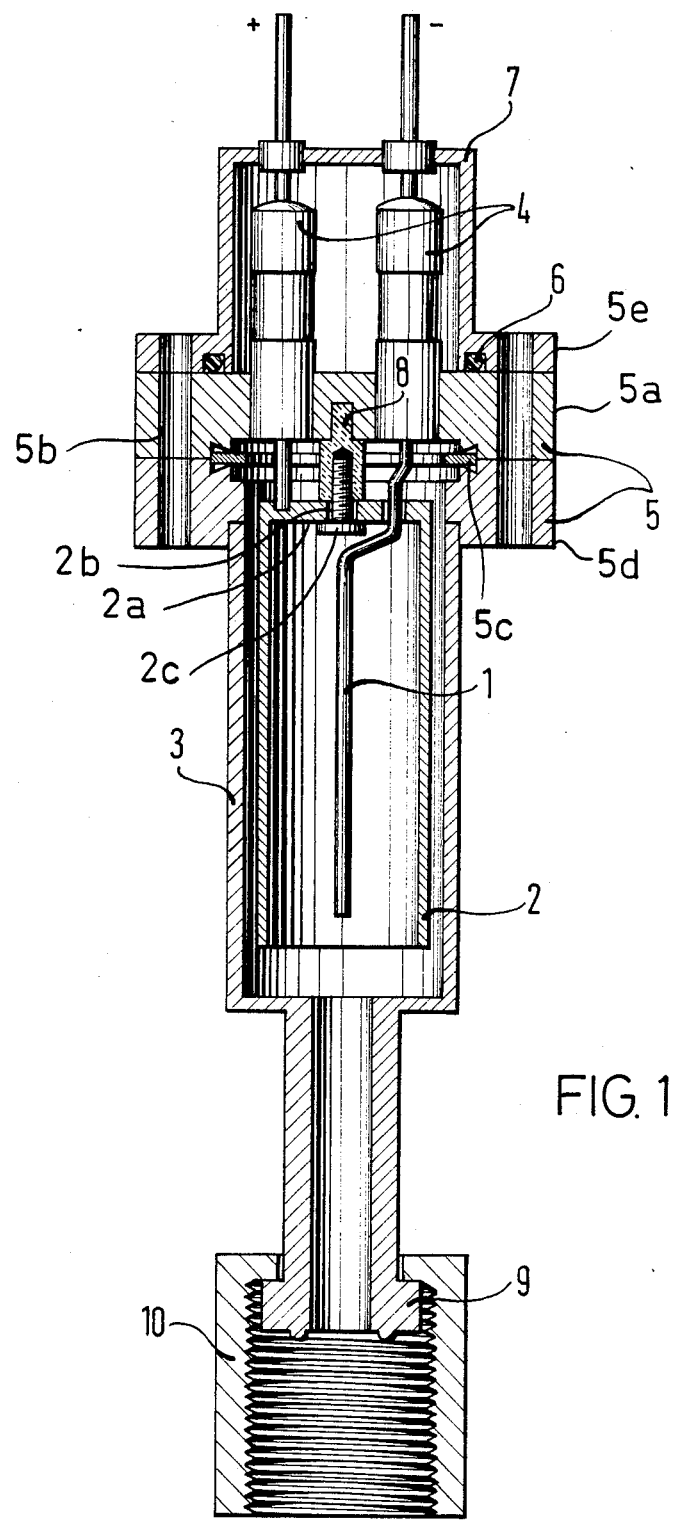
FIG. 1 is an axial cross sectional view through a measuring head for a device for the determination of tritium pressure in accordance with the invention.

FIG. 1 shows the basic elements of a measuring head for the measurement of tritium pressure according to the invention. This measuring head comprises a negatively charged inner axial electrode 1 which is comparatively thin and has small exposed surface areas. Surrounding this electrode is a positive cylindrical outer electrode 2, both electrodes being mounted in a housing and being connected through appropriate connectors via ceramic inserters 4 through a voltage source as described in connection with FIG. 3.

The inner electrode 1 is preferably composed of stainless steel and has a diameter of 1 mm while the outer electrode 2 can be a copper cylinder with an inner diameter of 12 mm. The outer electrode 2 has a base 2a traversed by a hole 2b through which passes a screw 2c releasably securing this electrode a ceramic post 8 anchored in a flange 5a of a flange system 5 which consists of ultrahigh vacuum flanges (CF 16 Leybold). These flanges are traversed by bolt bores 5b enabling the assembly to be mounted in a unit in which the tritium pressure is to be measured.

The flange 5a is sealed against a disc 5c and against a counterflange 5d which the flange 5e of a cap 7 is sealed against the flange 5a by an O-ring 6. The cap 7 protects the ceramic terminals 4 and constitutes an additional housing restricting tritium leakage into the environment. The ceramic post 8 which can be threaded into the flange 5a serves to insulate the copper cylinder from a housing 3 which is welded to the flange 5d. An ultrahigh vacuum coupling 9 of the Cajon/Best type is likewise provided and can be utilized to connect the measuring head to the gas-containing vessel 10 in which the pressure measurement is to be taken.

Figure 3:
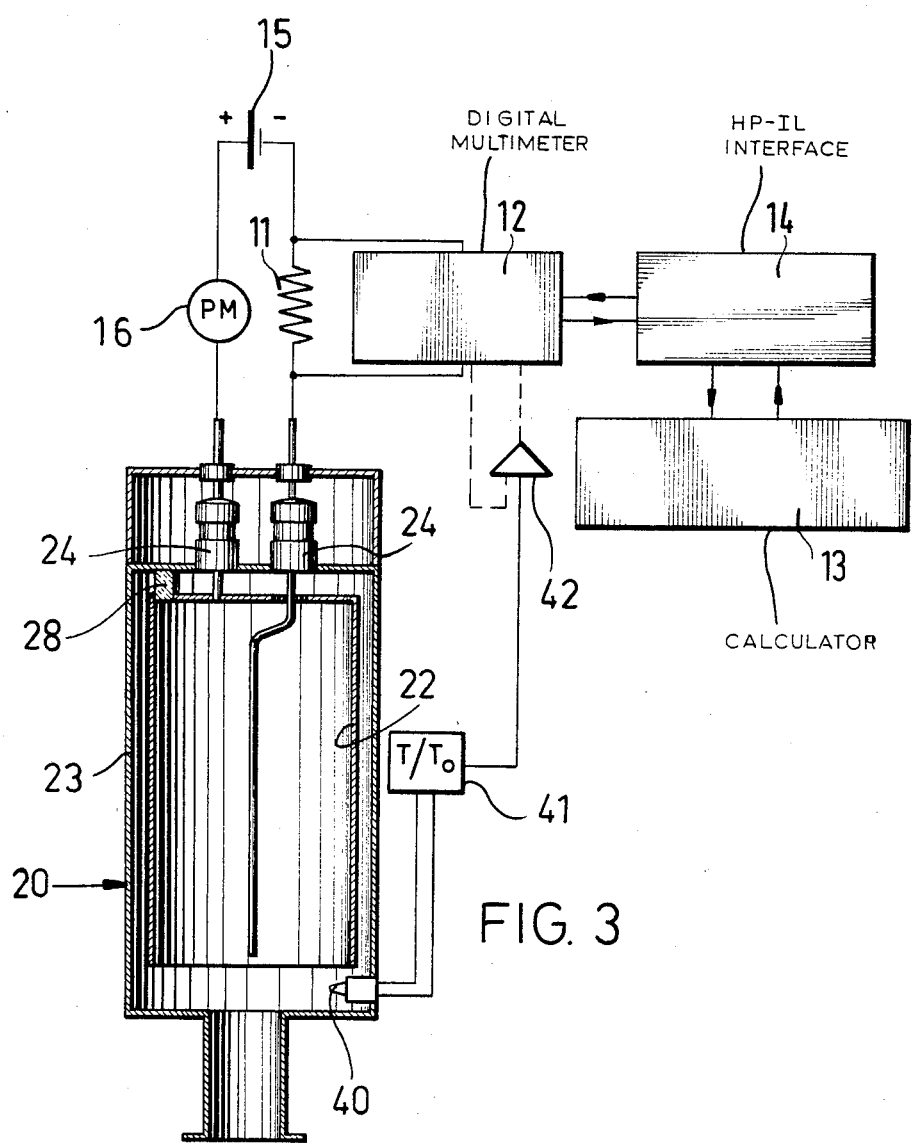
FIG. 3 is a block diagram of a circuit for use with such a measuring device.

In FIG. 3 we have shown a head 20 which utilizes the same principle as the head of FIG. 1. The cylinder 22 (FIG. 3) is fixed in place to the housing 23 by an insulator 28 and the ceramic insulators 24 through which the terminals pass are similar to the ceramic feedthrough insulators of FIG. 1. The circuitry includes a source 15 contributing a low voltage (up to 200 V) sufficient to apply a negative polarity to the central electrode and a positive polarity to the cylindrical electrode. A picoampere meter 16 can be provided in a circuit with the electrodes although, in addition or alternatively, it is desirable to connect a high ohmic resistor 11 in circuit with the electrodes and to measure the potential drop thereacross by a high-precision voltmeter 12. Preferably, the voltmeter 12 is a digital multimeter such as the Hewlett Packard HP 3468 A. A pocket computer such as Hewlett Packard HP 41 C can be provided as indicated at 13 and can be connected to the digital multimeter 12 by an appropriate interface such as a HP-IL-Interface 14 (Hewlett Packard HP 82160 A) so that the x-register of the HP 41 C receives a voltage value determined by the pressure value in the housing 23. This pressure value is transmitted as a data or pulse count via the HP-IL-bus to the digital multimeter in accordance with the previously determined calibration curve stored in the calculator so that the display of the multimeter indicates the tritium pressure directly. This process operates in an endless loop with the pocket calculator so that the multimeter always displays the actual tritium pressure.

Figure 2:
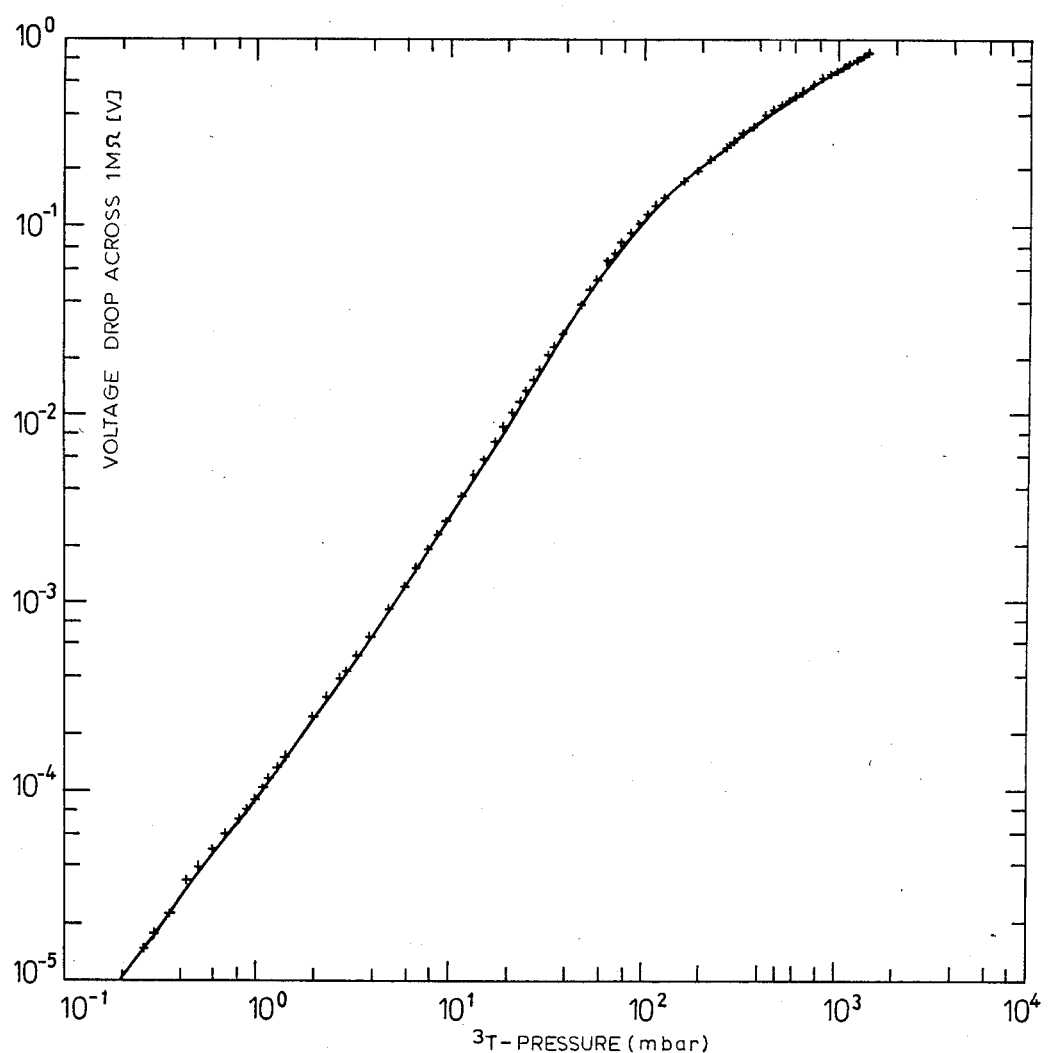
FIG. 2 shows a calibration curve for such a device.

FIG. 2 shows the calibration curve which is generated and is used to produce the output representing the pressure from the measured voltage. The calibration curve can be formed by detection of the voltage at a given temperature with known pressures and can be stored in the memory of the calculator so that direct display of the pressure can be effected at the multimeter. The characteristic curve of FIG. 2 is divided into 12 segments with the curve in each segment being approximated by an analytical function of the measured values.

Relative errors between the pressure values determined in accordance with the invention and by the more costly capacitive pressure sensors are less than 0.5% for pressures greater than 7 mbar.

The signal evaluation in accordance with the invention can thus be effected by components which are multifunctional such as the aforementioned digital voltmeter and pocket calculator and hence which are relatively inexpensive. The system can also be equipped with a conventional printer, for example the Hewlett Packard HP 82162 A to print out the measured values, e.g. directly as pressure measurements.

Figure 4:
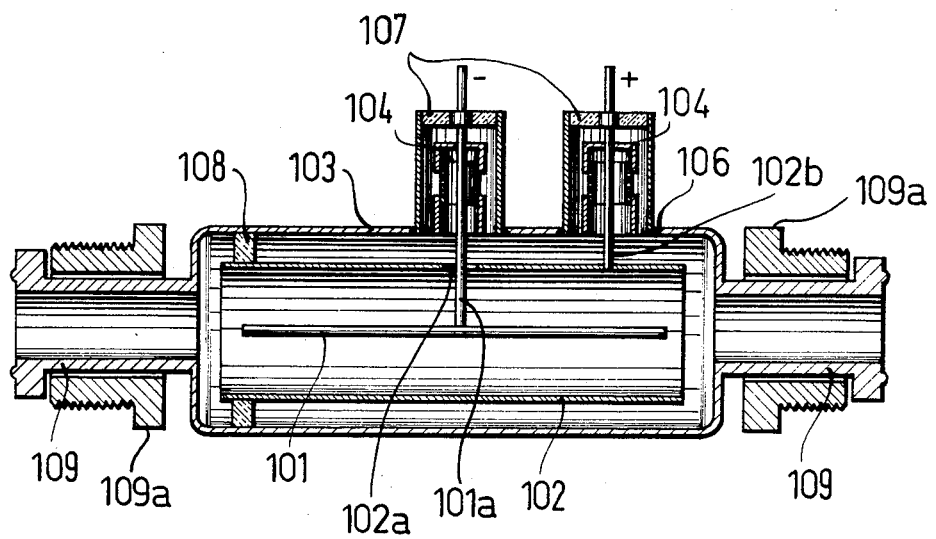
FIG. 4 shows a measuring head for in-line measurements utilizing the same principles.

In FIG. 4, we have shown an in-line or flow-through pressure measuring apparatus embodying the principles of the present invention in which similar reference numerals in one-hundred series represent similar functioning elements to those bearing the corresponding numerals in FIG. 1. In this embodiment, however, a pair ultrahigh vacuum sealing fittings 109 can be clamped in a pipeline by respective threaded members 109a while the housing 103 is a cylindrical body coaxial with the fitting 109 at opposite ends thereof so that a gas can flow through this housing. Within the housing, the cylindrical electrode 102 is positioned by a ceramic insulating ring 108 so as to be coaxial with the flow and with the housing, while the thin electrode 101 is a wire coaxial with the electrode 102 but provided midway of its length with a stem 101a passing through a ceramic insulator 104 suspending the electrode 101 with the electrode 102. The latter is formed with a hole 102a traversed by the stem 101a and is connected at its end remote from the ceramic ring 108 with a lead 102b extending through another ceramic insulator 104. The ceramic insulators 104 are enclosed by respective cup-shaped housings 107 which are sealed at 106 to the housing 103.

When the circuitry previously described is connected to the leads 101a and 102b, the measuring unit shown in FIG. 4 functions in the manner already described to provide a measurement of tritium pressure and especially tritium partial pressure.

When a thermocouple 40 (FIG. 3) is used to measure the temperature of the gas, this temperature can be applied to a quotient-forming unit 41 producing an output which is proportional to the value $T/T_o$. This output can be applied to a voltage-controlled amplifier 42 which can be coupled with the digital multimeter 12 to multiply the measured voltage by the correction factor for temperature as previously described, T representing the measured temperature while $T_o$ is the standardization or calibration temperature.

We claim:

1. An apparatus for measuring the pressure of a gaseous radioactive isotope which comprises:
   a housing provided with a fitting for connection of the housing to a source of said radioactive isotope;
   a cylindrical positive electrode received in said housing;
   a thin negative axial electrode surrounded by said cylindrical electrode and coaxial therewith;
   a source of direct current having a voltage of up to 200 V connected across said electrodes and forming an electric circuit therewith maintaining said cylindrical electrode relatively positive and said axial electrode relatively negative;
   means responsive to an electric current in the picoampere range connected to said circuit for indicating the pressure of said gaseous radioactive isotope in said housing;
   means for measuring the temperature of said gaseous radioactive isotope; and
   means responsive to the measured temperature for forming a quotient $T/T_o$ for control of an amplifier with a corresponding amplification to compensate for a difference between a measured temperature T and a calibration temperature $T_o$.

2. The apparatus defined in claim 1 which is utilized for partial pressure measurements of the gaseous radioactive isotope in the presence of high concentrations of other gases.

3. The apparatus defined in claim 1 wherein said means responsive to electric current includes a high ohmic resistor in said circuit and a voltmeter connected across said resistor for measuring potential drop thereacross.

4. The apparatus defined in claim 3 wherein said housing is tubular and is provided with such a fitting at each end for traversal by said gaseous radioactive isotope.

5. The apparatus defined in claim 3 wherein said housing is sealed with a flange structure at one end and is provided with said fitting at the opposite end.

6. The apparatus defined in claim 3 for the measurement of pressure of tritium gas wherein said electrodes have a spacing between substantially 2 and 10 mm.

7. The apparatus defined in claim 6 wherein said spacing is between substantially 4 and 6 mm.

8. The apparatus defined in claim 3 wherein said source has a voltage between substantially 80 and 120 volts.

9. The apparatus defined in claim 3 wherein said resistor has a resistance of substantially 1 megohm and said voltmeter is a digital voltmeter.

10. The apparatus defined in claim 3 wherein said housing, said electrodes and said fitting form a measuring head, all parts of which are constituted from material capable of withstanding temperatures of at least 250° C.

11. The use of the apparatus defined in claim 1 for measuring the pressure of tritium.

12. The apparatus defined in claim 1, further comprising means provided with a calibration curve connected to said means responsive to electric current for calibrating an output in accordance with characteristic data for a particular gaseous radioactive isotope of interest.

13. The apparatus defined in claim 1 wherein said means responsive to electric current is a picoampere meter connected in said circuit.

14. The apparatus defined in claim 13 wherein said housing is tubular and is provided with such a fitting at each end for traversal by said gaseous radioactive isotope.

15. The apparatus defined in claim 14 wherein said housing is sealed with a flange structure at one end and is provided with said fitting at the opposite end.

16. The apparatus defined in claim 13 for the measurement of pressure of tritium gas wherein said electrodes have a spacing between substantially 2 and 10 mm.

17. The apparatus defined in claim 16 wherein said spacing is between substantially 4 and 6 mm.

18. The apparatus defined in claim 13 wherein said source has a voltage between substantially 80 and 120 volts.

19. An apparatus for measuring the pressure of a gaseous radioactive isotope which comprises:
   a housing provided with a fitting for connection of the housing to a source of said radioactive isotope;
   a cylindrical positive electrode received in said housing;
   a thin negative axial electrode surrounded by said cylindrical electrode and coaxial therewith;
   a source of direct current having a voltage of up to 200 V connected across said electrodes and forming an electric circuit therewith maintaining said cylindrical electrode relatively positive and said axial electrode relatively negative;
   means responsive to an electric current in the picoampere range connected to said circuit for indicating the pressure of said gaseous radioactive isotope in said housing; and
   means provided with a calibration curve connected to said means responsive to electric current for calibrating an output in accordance with characteristic data for a particular gaseous radioactive isotope of interest.

20. The apparatus defined in claim 19 wherein said means responsive to electric current is a picoampere meter connected in said circuit.

21. The apparatus defined in claim 19 wherein said means responsive to electric current includes a high ohmic resistor in said circuit and a voltmeter connected across said resistor for measuring potential drop thereacross.

22. The apparatus defined in claim 21 wherein said housing is tubular and is provided with such a fitting at each end for traversal by said gaseous radioactive isotope.

23. The apparatus defined in claim 21 wherein said housing is sealed with a flange structure at one end and is provided with said fitting at the opposite end.

24. The apparatus defined in claim 21 for the measurement of pressure of tritium gas wherein said electrodes have a spacing between substantially 2 and 10 mm.

25. The apparatus defined in claim 21 wherein said source has a voltage between substantially 80 and 120 volts, said resistor has a resistance of substantially 1 megohm and said voltmeter is a digital voltmeter, and said housing, said electrodes and said fitting form a measuring head, all parts of which are constituted from material capable of withstanding temperatures of at least 250° C.

* * * * *